United States Patent [19]

Bergeron et al.

[11] Patent Number: 5,773,027
[45] Date of Patent: Jun. 30, 1998

[54] LIPOSOMES ENCAPSULATING ANTIVIRAL DRUGS

[75] Inventors: Michel G. Bergeron, Sillery; André Desormeaux, Neufchatel, both of Canada

[73] Assignee: Michael G. Bergeron, Sillery, Canada

[21] Appl. No.: 538,457

[22] Filed: Oct. 3, 1995

Related U.S. Application Data

[63] Continuation-in-part of Ser. No. 316,735, Oct. 3, 1994, abandoned.

[51] Int. Cl.$^6$ ............................ A61K 9/127; C07H 31/70
[52] U.S. Cl. ............................................ 424/450; 514/934
[58] Field of Search ............................ 424/450; 514/934

[56] References Cited

U.S. PATENT DOCUMENTS

| | | | |
|---|---|---|---|
| 4,235,871 | 11/1980 | Papahadjopoulos et al. | 424/19 |
| 4,416,872 | 11/1983 | Alving et al. | 424/177 |
| 5,225,212 | 7/1993 | Martin et al. | 424/450 |
| 5,254,539 | 10/1993 | Mitsuya et al. | 514/46 |

FOREIGN PATENT DOCUMENTS

| | | |
|---|---|---|
| WO88/07854 | 10/1988 | WIPO . |
| WO89/03220 | 4/1989 | WIPO . |
| WO90/14074 | 11/1990 | WIPO . |
| WO93/19738 | 10/1993 | WIPO . |

OTHER PUBLICATIONS

Bonnie Bean, "Antiviral Therapy: Current Concepts and Practices", *Clinical Microbiology Reviews*, vol. 5, No. 2, pp. 146–182, (Apr. 1992).

Andre Desormeaux, et al., "Antiviral efficacy, intracellular uptake and pharmacokinetics of free and liposome–encapsulated 2',3'–dideoxyinosine", *Current Science Ltd.*, vol. 8, No. 11, pp. 1545–1553, (1994).

M C Woodle, et al., "Versatility in lipid compositions showing prolonged circulation with sterically stabilized liposomes", *Biochimica et Biophysica Acta*, 1105, pp. 193–200, (1992).

Bakker–Woudenberg et al., "Increased Efficacy of Ganciclovir and Foscarnet Inhibition of Cytomegalovirus Replication in Vitro by Encapsulation in Liposomes", *Scand. J. Infect. Dis.*, 74, 54–57 (1991).

Deutsch et al., "Liposomal—Azidothimidine (AZT) in Advanced HIV Disease", *Can. J. Infect. Dis.*, 4, Suppl. B, 27B (1993).

Diaz–Llopis et al., "Liposomally–entrapped ganciclovir for the treatment of cytomegalovirus retinitis in AIDS patients", *Documenta Ophthalmologica*, 82, 297–305 (1992).

Embretson et al., "Massive covert infection of helper T lymphocytes and macrophages by HIV during the incubation period of AIDS", *Nature*, 362, 359–362 (1993).

Fox et al., "HIV in infected lymph nodes", *Nature*, 370, 256 (1994).

Gabizon et al., "Liposome formulations with prolonged circulation time in blood and enhanced uptake by tumors", *Proc. Natl. Acad. Sci. USA*, 85, 6949–6953 (1988).

Gendelman et al, "The macrophage in the persistance and pathogenesis of HIV infection", *AIDS*, 3, No. 8, 475–495 (1989).

Klibanov et al., "Amphipathic polyethyleneglycols effectively prolong the circulation time of liposomes", *FEBS Letters*, 268, No. 1, 235–237 (1990).

Mayer et al., "Techniques for Encapsulating Bioactive Agents into Liposomes", *Chemistry and Physics of Lipids*, 40, 333–345 (1986).

Meltzer et al., "Role of Mononuclear Phagocytes in the Pathogenesis of Human Immunodeficiency Virus Infection", *Annu. Rev. Immunol.*, 8, 169–194 (1990).

Pantaleo et al., "HIV infection is active and progressive in lymphoid tissue during the clinically latent stage of disease", *Nature*, 362, 355–358 (1993).

Phillips et al., "Liposomal Encapsulation of Azidothymidine Results in Decreased Hematopoietic Toxicity and Enhanced Activity Against Murine Acquired Immunodeficiency Syndrome", *Blood*, 79, No. 5, 1137–1143 (1992).

Szoka et al., "Procedure for preparation of liposomes with large internal aqueous space and high capture by reverse–phase evaporation", *Proc. Natl. Acad. Sci. USA*, 75, No. 9, 4194–4198 (1978).

*Primary Examiner*—Gary L. Kunz
*Attorney, Agent, or Firm*—Schwegman, Lundberg, Woessner & Kluth, P.A.

[57] ABSTRACT

A method is disclosed for the treatment of viral diseases comprising the administration of antiviral agents encapsulated in liposomes. Also provided are formulations of liposomes for the treatment of viral diseases and more particularly for the treatment of infections caused by viruses like human immunodeficiency virus (HIV) and cytomegalovirus (CMV). These formulations of liposomes are composed of specific classes of lipid components and contain an entrapped drug effective against the viral disease. These liposomal formulations of antiviral drugs allow high cellular penetration in different cell lines, good in vitro antiviral efficacy against HIV and CMV replication, efficient in vivo targeting of HIV reservoirs and a marked improvement of the pharmacokinetics of drugs.

20 Claims, 11 Drawing Sheets

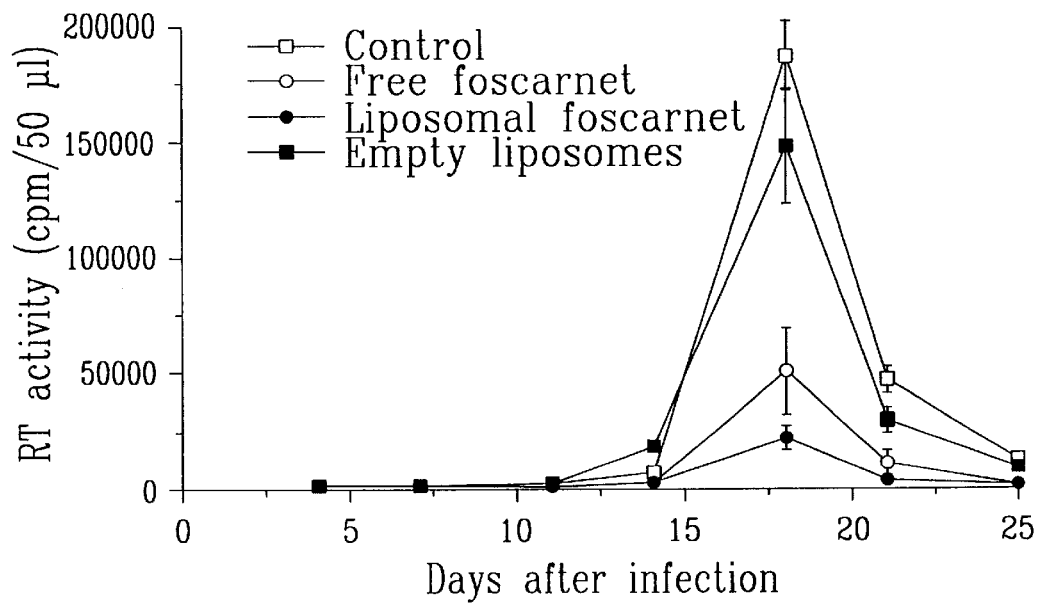
FIG_2E
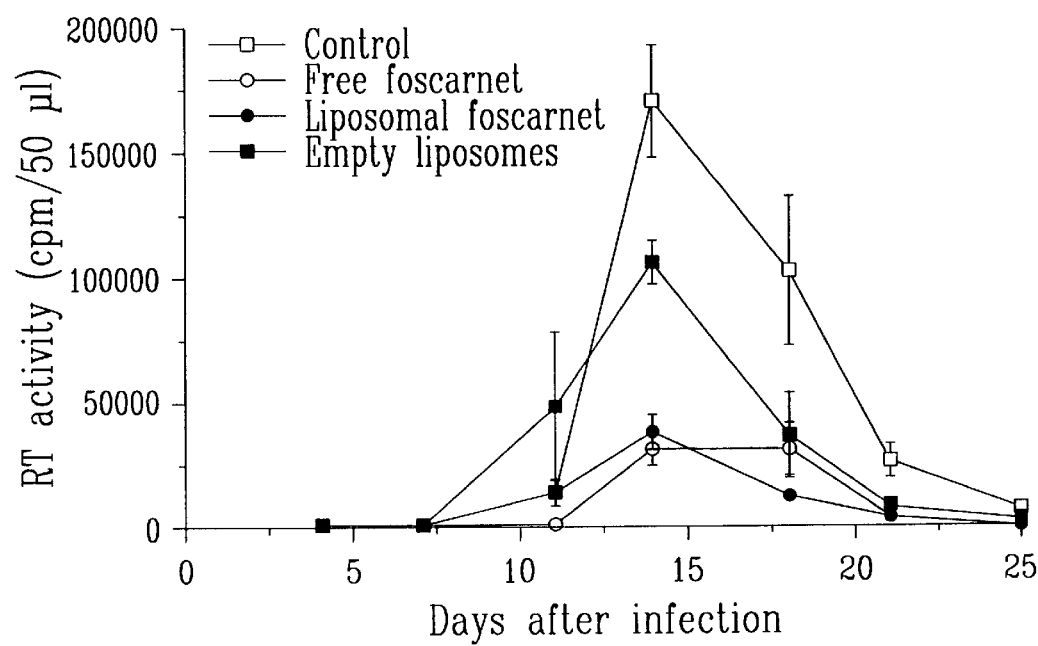
FIG_2F

LIPOSOMES ENCAPSULATING ANTIVIRAL DRUGS

CROSS-REFERENCE TO RELATED APPLICATION

This application is a continuation-in-part of U.S. application Ser. No. 08/316,735, filed Oct. 3, 1994 now abandoned.

FIELD OF THE INVENTION

This invention relates to formulations of liposomes and method for use in the treatment of viral diseases and particularly in the treatment of infections caused by viruses like human immunodeficiency virus and cytomegalovirus.

BACKGROUND OF THE INVENTION

Many antiviral agents have been developed for the treatment of patients with human immunodeficiency virus (HIV) infection. However, only temporary and limited benefits are observed in HIV-infected patients treated with any of the actual antiretrovirals or combinations of them. The limited ability of these agents to decrease viral burden, the rapid development of resistance and the toxic side-effects of most drugs have limited their long-team efficacy. One major problem associated with the administration of antiviral agents to patients is their poor ability to penetrate and target infected cells. Rapid drug clearance and the toxicity of parent compounds or metabolites constitute also some of the major drawbacks which may slow down the development and use of many antiviral agents. Given the severe toxicity of antiviral agents actually available to treat AIDS and other viral diseases and their limited ability to target infected cells, strategies aimed at reaching therapeutic levels of drugs into infected cells and reducing toxicity should be explored. Entrapment of drugs into liposomes constitutes an attractive approach to improve the delivery of active agents to infected cells and to reduce toxic effects associated with their administration. Liposomes are microscopic vesicles in which a variety of drugs can be incorporated. Because of the similarity of the primary components of liposomes with natural membranes, liposomes are generally non-toxic and biodegradable. We believe that a better understanding of the role of liposomes as carriers of antiviral agents may lead to new strategies which way improve the efficacy and safety of drug used for the treatment of AIDS and other viral diseases.

There is now much evidence showing that macrophages play a central role in HIV pathogenesis, acting as reservoirs for dissemination of virus throughout the immune system (Gendelman et al., 1989, AIDS 3:475–495; Meltzer et al., 1990, Ann. Rev. Immunol. 8:169–194). It was recently reported that in the early-stage of the infection and throughout the clinically latent stage, HIV accumulates and replicates actively in the lymphoid organs despite a minimal viral activity in peripheral blood (Pantaleo et al., 1993, Nature 362:355–358; Embretson et al., 1993, Nature 362:359–362; Fox et al., 1994, Nature 370:256). The high viral burden observed in the lymphoid tissues was reported to be associated to trapped HIV particles in the follicular dendritic cells of the germinal centers. Over the course of HIV infection, the follicular dendritic cells network was gradually disrupted and ultimately destroyed. As the microenvironment of lymphoid tissues is crucial for effective immune response, it is primordial to reduce or abrogate the accumulation of HIV into the lymphoid tissues in order to preserve the integrity of the microenvironment network. The use of liposomes as a drug delivery system is particularly relevant to control the progression of HIV disease. Since liposomes are naturally taken up by cells of the mononuclear phagocyte system (MPS), liposome-based therapy should concentrate the antiviral agents within cells susceptible to HIV infection and, at the same time, reduce the quantity of drugs at sites where it might be potentially toxic. Liposome-encapsulated drugs could therefore represent a convenient strategy to reduce the dissemination of HIV to the lymphoid tissues and preserve the follicular dendritic cells microenvironment that will likely protect the infected host from developing the characteristic immunodeficient state.

The use of liposomes as drug delivery system could offer important benefits when compared to the parent drug. For instance, liposomes could protect drugs against enzymatic degradation, improve their pharmacokinetics and tissue distribution and may allow a controlled release of therapeutic agents to appropriate cells. In addition, the distribution and therapeutic availability of liposomes can be modulated through variations of their size, lamellarity, lipid composition, charge and surface properties. It is thus primordial to adapt the physicochemical properties of liposomes with the desired therapeutic objective. It is an object of the present invention to generate liposomal formulations of drugs for the treatment of AIDS and other viral diseases. Such targeted delivery system should hopefully result in an increased efficacy and reduced toxicity of antiviral agents in humans suffering from AIDS or other viral diseases. In addition, the improved drug bioavailability upon encapsulation of drugs into liposomes could reduce the dosing interval and consequently improve the quality of life of patients infected with HIV and other viruses.

SUMMARY OF THE INVENTION

The invention relates to a method for the treatment of viral diseases comprising the administration of antiviral agents encapsulated in liposomes. The invention also concerns formulations of liposomes for the treatment of viral diseases and more particularly for the treatment of infections caused by viruses like HIV and CMV. The formulations of liposomes are composed of specific classes of lipid components and contain an entrapped drug effective against the viral disease. The originality of the present invention is that these liposomal formulations of drugs allow high cellular penetration in different cell lines, good in vitro antiviral activity against HIV and CMV, efficient in vivo targeting of HIV reservoirs and a marked improvement in the pharmacokinetics of drugs (see Examples).

In a preferred embodiment, formulations of liposomes are composed of distearoylphosphatidylcholine (DSPC) :distearoylphosphatidylglycerol (DSPG) in a molar ration of 10:3, have a mean particle diameter between about 0.05 and 0.5 $\mu$m, and contain 2'–3'-dideoxyinosine (ddI) as an antiviral drug. In another preferred embodiment, formulations of liposomes are composed of DSPC:DSPG:distearoylphosphatidylethanolamine-polyethyleneglycol (DSPE-PEG) in a molar ration of 10:3:1.45, have a mean particle diameter between about 0.05 and 0.5 $\mu$m, and contain 2'–3'-dideoxyinosine (ddI) as an antiviral drug. In another preferred embodiment, polyethyleneglycol has a molecular weight between about 500 and 5000 daltons. In another preferred embodiment, formulations of liposomes are composed of dipalmitoylphosphatidylcholine (DPPC):dicetylphosphate (DP):cholesterol (CHOL) in a molar ratio of 4:1:5, have a mean particle diameter between about 0.05 and 0.5 $\mu$m, and contain 2'–3'-dideoxycytidine (ddC) as an antiviral drug. In still another preferred embodiment, formulations of liposomes are composed of DPPC:dipalmitoylphosphatidylglycerol (DPPG) in a molar ration of 10:3, have a mean particle diameter between about 0.05 and 0.5 µm, and contain foscarnet as an antiviral drug.

BRIEF DESCRIPTION OF THE DRAWINGS

FIGS. 2c and 2e show the antiviral activity of free and liposomal ddC and foscarnet, respectively, in Molt-4 clone-8 cells infected with HIV-$1_{IIIB}$. FIG. 2f shows the antiviral activity of free and liposomal foscarnet in Supt-1 cells infected with HIV-$1_{IIIB}$.

DETAILED DESCRIPTION OF THE INVENTION

Lipid components

Figure 1A:
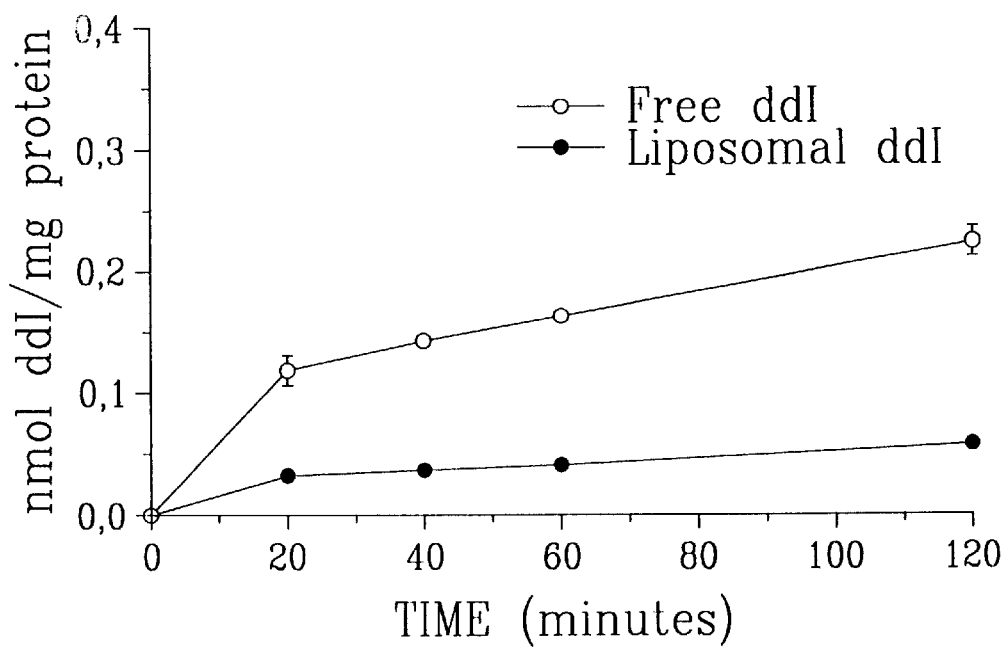
FIGS. 1a and 1b illustrate the accumulation of free and liposomal ddI and ddC, respectively, as a function of time, in U937 cells (Panel A) and RAW 264.7 cells (Panel B).

In liposome-based products, it is necessary to use liposome bilayer characteristics which allow high efficiency of drug encapsulation as well as reduced leakage of entrapped drug to take advantage of the ability of liposomes to deliver high quantity of antiviral agents into infected cells. In the case of the drugs under the scope of this invention, these requirements are obtained by using liposomes composed of i) a mixture of diacylphosphatidylcholine and diacylphosphatidylglycerol (in a molar ranging between 10:1 and 1:1) wherein the acyl chains are either saturated or unsaturated and have between 14 and 18 carbon atoms in length or ii) a mixture of diacylphosphatidylcholine:dicetylphosphate:cholesterol in a molar ratio of 4:1:5 wherein the acyl chains of phosphatidylcholine are either saturated or unsaturated and have between 14 and 18 carbon atoms in length.

The liposomes of the present invention include sterically stabilized liposomes, defined herein as, liposomes composed of the lipid components mentioned above and which are modified by the incorporation of polymers, such as poloxamers and poloxamines, or of amphipathic lipids derivatized with a polymer such as DSPE-PEG or dioleoylphosphatidylethanolamine-PEG (DOPE-PEG). Details for the synthesis of DSPE-PEG are provided in Example 1. The liposomes of the present invention also include immunoliposomes, defined herein as, liposomes or sterically stabilized liposomes composed of the lipid components mentioned above and which are modified by the coupling of antibody molecules which enhance the targeting of specific cells.

Not all the liposomal formulations tested have shown efficient drug encapsulation and drug retention. For instance, the entrapment of ddI in liposomes composed of egg phosphatidylcholine:cholesterol in a molar ration of 55:45 showed an efficiency of drug encapsulation which was about 30 times lower than that observed for liposomes composed of DSPC:DSPG in a molar ratio of 10:3. On the other hand, over 90% of ddI was released from multilamellar vesicles composed of egg PC:cholesterol:cardiolipin in a molar ration of 35:45:10 after only 1 hour of incubation in human serum. In contrast, only 10% of ddI was released from multilamellar vesicles composed of DSPC:DSPG in a molar ration of 10:3 in similar conditions after 5 hours of incubation in human serum.

Even though the following examples described specific liposomal formulations, it is deemed that a family of liposomal formulations can be easily derived therefrom, without affecting the valuable properties thereof. Therefore, this family of compounds comprises other acyl chains of given phospholipids formulations that have been tested in the practice.

Preparation of liposomes

A large number of techniques of preparation of liposomes has been developed in the past few years in response to the growing number of specific applications of liposomes as drug delivery system. The preparation of liposomes in the present invention can be done by a variety of techniques such as those described in the literature (Szoka and Papahadjopoulos, 1980, Ann. Rev. Biophys. Bioeng. 9:467–508; Nässander et al., 1990, Liposomes in Biodegradable polymers as drug delivery systems. p.261–338). Among them, the thin lipid film hydration technique constitutes a rapid and simple procedure to generate liposomes. Liposomes generated by this technique are mostly multilamellar vesicles and generally range in size from 0.2 to 10 µm. The thin lipid film hydration technique is detailed in Example 2. Another common technique of preparation of liposomes is the reverse phase evaporation technique described by Szoka et al. in U.S. Pat. No. 4,235,871. Liposomes generated by this technique are unilamellar or plurilamellar and generally range in size from 0.2 to 5 µm. The reverse phase evaporation technique is detailed in Example 3.

Antiviral agents

Any inhibitor of viral DNA and/or RNA synthesis and/or HIV protease is under the scope of this invention. Included in this class are antiviral agents such as 3'-azido-3'-deoxythymidine (AZT), ddI, ddC, foscarnet, ribavirin, ganciclovir and saquinavir. Incorporation of these drugs into liposomes can be achieved by one or more methods of active and/or passive loading such as those described in the literature (Mayer et al., 1986, Chem. Phys. Lipids 40:333–345)

Formulations of liposomes of the present invention include those having a mean particle diameter of any size but most preferably those between about 0.05 and 0.5 μm. The formulations of liposomes of the present invention also include those prepared with any drug/lipid molar ratio. As previously mentioned, the propensy of liposomes to be taken up by cells of the MPS should concentrate the entrapped antiviral agents within cells susceptible to HIV or other viral infections, improving therefore their antiviral efficacy and reducing their toxicity. Therefore, the following examples are intended to demonstrate the preparation of specific liposomal formulations of antiviral drugs which could be very efficient for the treatment of HIV and CMV infections, but are in no way intented to limit the scope thereof. In addition, even though the effect of liposomal formulations of drugs has been specifically verified on two viral species, HIV and CMV, any virus sensitive to the effect of inhibitors of viral DNA and/or RNA synthesis and/or HIV protease is under the scope of this invention.

EXAMPLE 1
Synthesis of DSPE-PEG

Distearoylphosphatidylethanolamine-polyethyleneglycol (DSPE-PEG) was prepared as previously describe (Gabizon and Papahadjpoulos, 1989, Proc. Natl. Acad. Sci. USA 85:6949–6953; Klibanov et al., 1990, FEBS Letters 268:235–237). Briefly, methoxypolyethyleneglycol succinimidyl succinate (PEG-OSu; MW 5000), DSPE and triethylamine in a molar ration of 3:1:3.5 containing 0.01 μCi of [$^{14}$C]-dioleoylphosphatidylethanolamime DOPE ([$^{14}$C]-DOPE) by μmol of lipid were incubated overnight at room temperature in CHCl$_3$. Solvent was then evaporated under a stream of nitrogen and the resulting dry mixture was hydrated with bidistilled water. The micelles solution was filtered through a column (32×2 cm) containing Bio-Gel A-1.5M (50–100 mesh) to remove uncoupled PEG-OSu. Peak fractions containing DSPE-PEG were determined by both scintillation countings (for [$^{14}$C]-DOPE-PEG) and absorbance readings at 225 nm (for free PEG-OSu). Fractions containing DSPE-PEG were pooled and dialysed for 24 hrs against water using dialysis membrane with a nominal molecular weight cut-off (MWCO) of 300,000 (Spectra-Por, Spectrum Medical, Los Angeles, Calif.) and then lyophilized. DSPE-PEG can be also obtained commercially in a variety of molecular weights.

EXAMPLE 2

2'–3'-dideoxyinosine (ddI) was encapsulated into liposomes composed of DSPC:DSPG in a molar ratio of 10:3 and DSPC:DSPG:DSPE-PEG in a molar ratio of 10:3:1.45 using the thin lipid film hydration. DSPE-PEG can be synthetized according to Example 1 or obtained commercially. In brief, the lipid mixture was dissolved in chloroform:methanol (2:1 v/v) in presence of a small proportion of [$^{14}$C]-DPPC (<0.002% mol/mol) and solvent was next evaporated in a round bottom flask to form a thin lipid film on the wall of the flask. The lipid film was then hydrated with a phosphate buffered solution (PBS, 145 mM, pH 7.4) of ddI in a drug/lipid molar ratio of 2 in which a small proportion of radiolabeled [$^3$H]-ddI was added. After approximately a 30 minutes stand at room temperature, multilamellar vesicles (MLVs) were formed upon mechanical agitation of the liposomal preparation at a temperature above the gel to fluid phase transition of the lipid mixture. MLVS were extruded with a stainless steel extrusion device (Lipex Biomembrane, Vancouver, BC) through polycarbonate membranes (Nuclepore, Cambridge, Mass.) of 0.2 μm. Vesicles size distribution and homogeneity were evaluated by quasi-elastic light scattering (QELS) with a submicron particle analyzer (model N4SD Coulter Electronics, Hialeah, Fla.). The mean diameter of the extruded liposomes was 0.175±0.035 μm and 0.15±0.01 μm for the DSPC:DSPG and DSPC:DSPG:DSPE-PEG formulations, respectively. Unencapsulated drug was removed either by centrifugation (300 g for 15 min at 4° C.) of the liposomal preparation (1 ml) through a 10 ml column of coarse Sephadex G-50 (Pharmacia LKB, Montreal, QC), ultracentrifugation (160000 g for 90 min at 4° C.) or by dialysis against a determined volume of PBS. Efficiency of drug entrapment has been determined with the use of a liquid scintillation counter (model LS 6000TA, Beckman Instruments Canada Inc., Mississauga, ON).

EXAMPLE 3

2'–3'-dideoxycytidine (ddC) was encapsulated into liposomes composed of DPPC:DP:CHOL in a molar ratio of 4:1:5 using the reverse phase evaporation method (Szoka and Papahadjopoulos, 1978, Proc. Natl. Acad. Sci. USA 75:4194–4198). In brief, the lipid mixture was dissolved in chloroform:methanol (2:1 v/v) in presence of a small proportion of cholesteryl [1-$^{14}$C] oleate and solvent was next evaporated in a round bottom flask to form a thin lipid film on the wall of the flask. The lipid film was than redissolved in isopropylether:methanol (3:0.8 v/v). To this organic phase was added a phosphate buffered solution (PBS, 145 mM, pH 7.4) of ddC in a drug/lipid molar ratio of 3.6 containing a small proportion of radiolabeled [$^3$H]-ddC. The mixture of the two phases was next sonicated for 5 min in an ultrasonic bath at room temperature to give an homogeneous solution. The organic solvent was eliminated under vacuum in controlled conditions by retroevaporation at 50° C. The liposome suspensions were then extruded through polycarbonate membranes of 0.4 μm. Vesicles size distribution and homogeneity were evaluated by QELS. The mean diameter of the extruded liposomes was 0.300±0.08 μm. Unencapsulated drug was removed as described above and encapsulation efficiency of ddC was estimated by radioactivity countings.

EXAMPLE 4

Foscarnet was encapsulated into liposomes using the reverse phase evaporation method as described for the liposomal preparation of ddC (Example 3) except that the lipid components was DPPC:DPPG in a molar ratio of 10:3. In this case, the drug/lipid molar ratio was 5, and [$^3$H]-DPPC and [$^{14}$C]-foscarnet were used as lipid and drug markers, respectively. The liposome suspensions were extruded through polycarbonate membranes of 0.2 μm generating liposomes with a mean diameter of 0.165±0.030 μm. Unencapsulated drug was removed as described above and encapsulation efficiency of foscarnet was estimated by radioactivity countings.

Examples comparing liposomal drugs with free drugs
Cellular uptake

We have performed in vitro experiments to evaluate the accumulation of free and liposome-encapsulated anti-HIV agents in murine monocyte-macrophage RAW 264.7 cells and in human premonocytoid U937 cells. In brief, experiments were performed by incubating confluent cells in culture medium in presence of different concentrations of free and liposome-encapsulated anti-HIV agents in which a small proportion of radiolabeled drugs and lipids were added. At different incubation times, the medium was removed and cells were washed and treated with a Triton X-100 solution. Drug and lipid uptake were determined by measuring the radioactivity level with a liquid scintillation counter. The protein concentration for each sample was determined with a Pierce bicinchoninic acid protein assay (Rockford, Ill.) in microtiter plates. Results showed that the incorporation of ddC in liposomes greatly enhanced the drug uptake in both RAW 264.7 and U937 cells (FIGS. 1b and 1c). Similarly, liposomal foscarnet accumulated much better than the free drug in RAW 264.7 cells (FIG. 1d). In contrast, although the uptake level of liposomal ddI in these cells was similar to that of liposomal formulations of ddC of foscarnet, a higher accumulation of free ddI was observed in both cell lines (FIG. 1a) suggesting a greater membrane permeability of these cell lines to ddI compared to the other anti-HIV agents.

In vitro antiviral efficacy

Figure 2A:
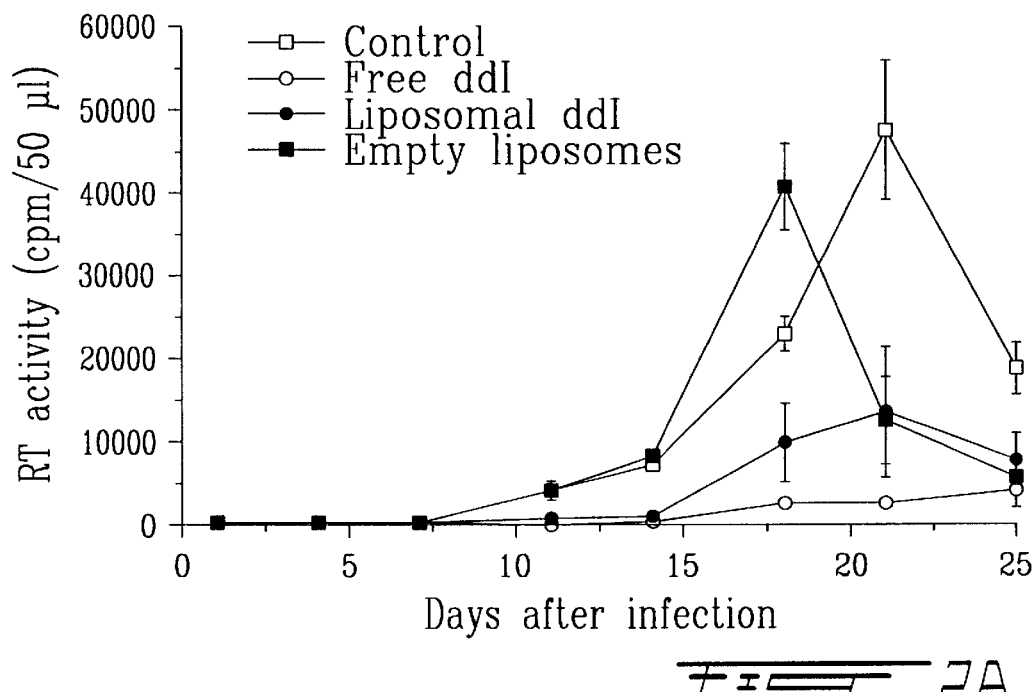
FIGS. 2a, 2b and 2d show the antiviral activity of free and liposomal ddI, ddC and foscarnet, respectively, in U937 cells infected with HIV-$1_{IIIB}$.
Figure 2B:
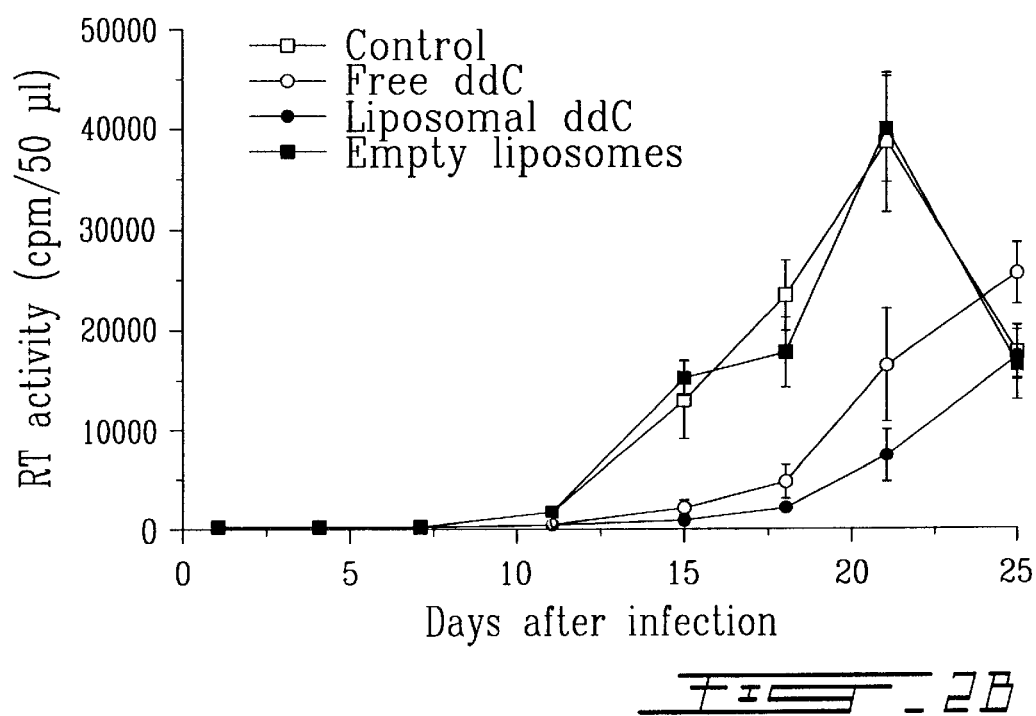
Figure 2C:
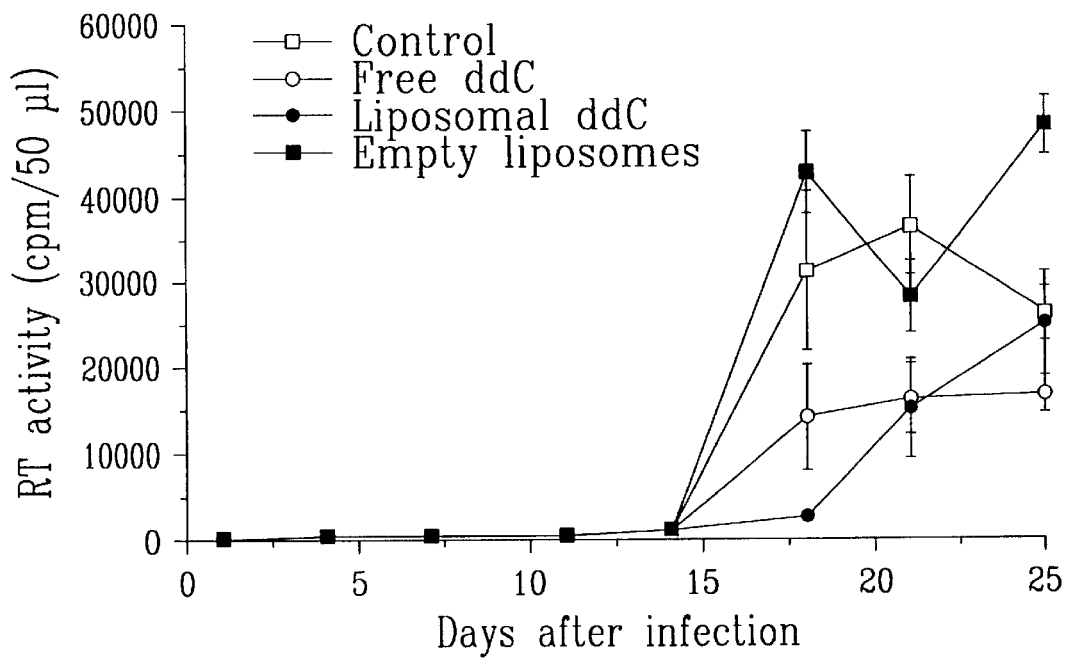
Figure 2D:
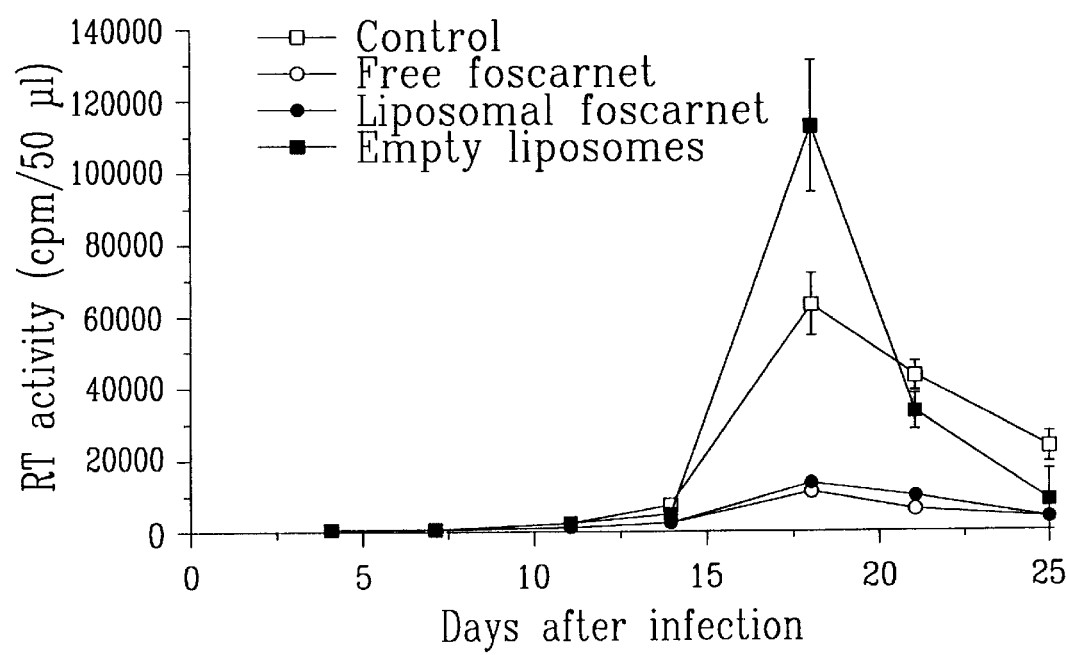

The antiviral efficacy of the liposomal formulations of antiviral drugs have also been evaluated in different cell lines. Briefly, cells were infected with different strains of HIV with a multiplicity of infection of 1 (virus/target cell) and were treated with different concentrations of free and liposome-encapsulated drugs. Virus replication were monitored at different time intervals by measuring either the reverse transcriptase activity in cell-free supernatants or the viral p24 protein using an enzymatic test. Virus transcription was also monitored by polymerase chain reaction (PCR) analysis 24 hours after treatment using an HIV primer pair (M661/M667). The PCR evaluation was normalized with respect to the amount of human β-globin gene in cells. Cell viability was assessed using a tetrazolium-based colorimetric (MTT) assay. Results showed that the incorporation of ddC in liposomes has resulted in comparable or even better anti-HIV efficacy than the free agent against HIV-1$_{IIIB}$ replication in U937 and Molt-4 clone-8 cells (FIGS. 2b and 2c). Similarly, liposomal foscarnet showed comparable or even better antiviral efficacy than that of the unencapsulated drug against HIV-1$_{IIIB}$ replication in U937, Molt-4 clone-8 and Supt-1 cells (FIGS. 2d, 2e, and 2f). Although the antiviral efficacy of the liposomal formulation of ddI was lower than that of the free agent against HIV-1$_{IIIB}$ replication in U937 cells (FIG. 2a), a greater anti-HIV efficacy was observed for liposomal ddI against HIV-1$_{Ada-M}$ replication in monocyte-derived macrophages (Table 1). It is appreciated that, as liposomes are preferentially taken up by cells of the MPS, the much higher anti-HIV efficacy of the liposomal drugs over the free drugs will be most likely observed under in vivo situations.

TABLE 1

Antiviral eficacy of free and liposomal ddI in primary monocyte-derived macrophages infected with HIV-1$_{Ada-M}$

| Treatment | Concentration (μM) | p24 (ng/ml) (Days post-infection) | | |
|---|---|---|---|---|
| | | 7 | 13 | 17 |
| Untreated | 0 | 161 | 1,263 | 7,700 |
| Liposomal ddI | 0.1 | 0 | 0 | 0 |
| | 1 | 0 | 0 | 0 |
| | 10 | 0 | 0 | 0 |

TABLE 1-continued

Antiviral eficacy of free and liposomal ddI in primary monocyte-derived macrophages infected with HIV-1$_{Ada-M}$

| Treatment | Concentration (μM) | p24 (ng/ml) (Days post-infection) | | |
|---|---|---|---|---|
| | | 7 | 13 | 17 |
| Free ddI | 0.1 | 0 | 20 | 280 |
| | 1 | 0 | 0 | 0 |
| | 10 | 0 | 0 | 0 |

Peripheral blood mononuclear cells were suspended in seeding medium in a 48 well-plate at a density of 3 × 10$^6$ cells/ml. Five days after initiation of the cultures, nonadherent cells were removed by rinsing the cultures four times with PBS. Adherent cells were first preincubated in the presence or absence of drug-containing medium for 2 hours prior to inoculation with 10,000 cpm/well of the Ada-M monocytotropic strain of HIV-1. Thereafter, medium was changed once every 4 to 5 days and was replaced with medium supplemented or not with ddI. Virus replication was monitored by measuring p24 levels using an enzymatic assay.

Figure 2G:
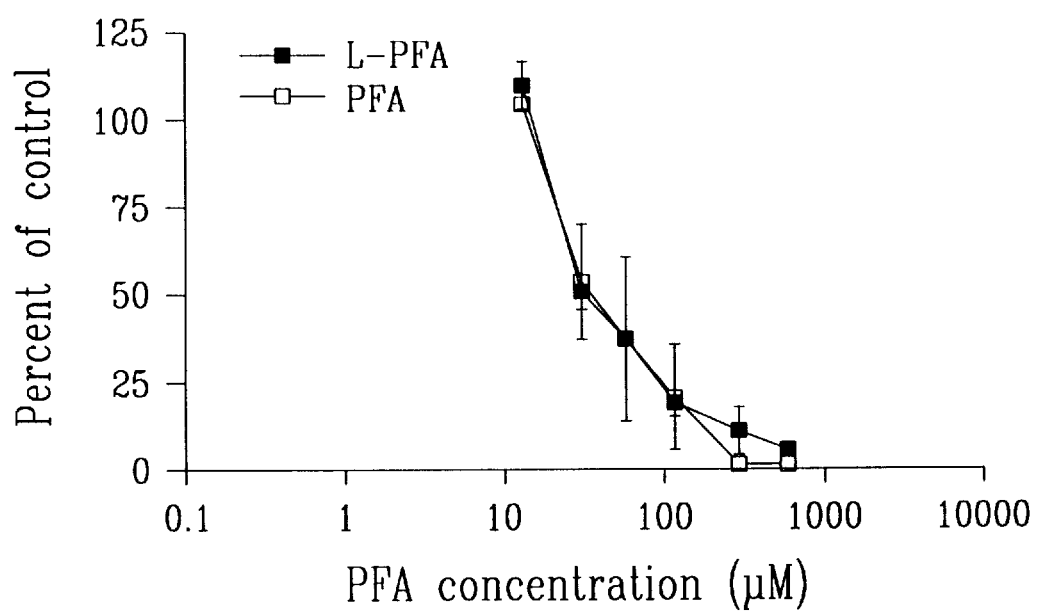
FIG. 2g shows the inhibition of CMV p72 protein expression in human lung fibroblast cells (MRC-5 cell line) by free and liposomal foscarnet.

The anti-CMV activity of free and liposome-encapsulated foscarnet has been also evaluated in embryonic lung fibroblast cells (MRC-5 cell line). In brief, cells were infected with the AD169 strain of human CMV and were treated with serial dilutions of free of liposomal foscarnet. After a 96 hours incubation, cells were fixed and immunoperoxydase staining was performed using a monoclonal antibody directed against a 72-kDa immediate early CMV protein Labeled plaques were counted and results were expressed as percent of untreated infected control cells versus concentration of foscarnet. Results showed that free and liposomal foscarnet have comparable inhibitory activity against CMV p72 protein expression in MRC-5 cell line (FIG. 2g).

In vivo studies

The pharmacokinetic properties and tissue distribution of free and liposome-encapsulated anti-HIV agents have been investigated in rats. In brief, free and liposome-encapsulated drugs were injected to female Sprague-Dawley rats as a single intravenous bolus dose via a catheter inserted through the jugular vein of animals. At specific time points, animals were sacrificed and blood was collected in heparinized tubes and separated by centrifugation. At the same time, selected tissues were removed, washed, weighed and homogenized. Tissues and plasma were then treated according to a commercial tissue solubilizer procedure. The determination of drug and lipid levels in all samples were monitored with radioactive tracers.

Results clearly showed that the encapsulation of the antiviral agents into liposomes resulted in a much higher drug accumulation in macrophage-rich tissues in respect to that observed for unencapsulated drugs (FIGS. 3a, 3b, 3c and 3d). The delivery of a greater amount of antiviral agents in these tissues susceptible to HIV infection and the reduced delivery of drugs at sites where it might be potentially toxic should result in an increased efficacy and reduced toxicity of the anti-HIV agents. Of particular interest, we showed that the accumulation of liposomal foscarnet in the lymph nodes was 8 times greater than that of free agent (Table 2; same formulation as in FIG. 3d). An increase drug accumulation was also observed in the brain of animals when liposomal foscarnet rather than the free agent was injected to animals. Such caracteristic is of prime importance as severe central nervous system diseases are involved in HIV pathology. In addition, as our data demonstrated an enhanced drug accumulation in the eyes after the injection of liposomal foscarnet rather than the free drug, administration of liposome-encapsulated foscarnet should improve the drug efficacy against CMV in patients infected with HIV and treated for CMV retinitis. Improved pharmacokinetics were also observed upon entrapment of the antiviral agents into liposomes (Tables 3 and 4; same formulations as in FIGS. 3a, 3b and 3d). The systemic clearance of the entrapped drugs was found to be much lower than that of the free agents, resulting in a large increase in the elimination half-life of the liposomal drugs. The improved pharmacology of the antiviral agents upon encapsulation in liposomes could hopefully reduce the dose of antiviral agents used in conventional therapy as well as the frequency of administration of the anti-HIV agents improving therefore the quality of life of patients with AIDS and other viral diseases.

TABLE 2

Area under the curve of free and liposome-encapsulated foscarnet in different tissues, following the administration of a single intravenous dose (10 mg foscarnet/kg) in rats.

| Tissues | Liposomal foscarnet | Free foscarnet | Ratio L-foscarnet/ free foscarnet |
|---|---|---|---|
| Lymph nodes | 163.5 | 20.3 | 8.1 |
| Brain | 40.8 | 3.1 | 13.2 |
| Eyes | 86.9 | 22.9 | 3.8 |
| Spleen | 1151.4 | 0.8 | 1495.3 |
| Liver | 62.5 | 1.2 | 52.1 |
| Lungs | 59.7 | 1.5 | 39.8 |

Values, expressed in nmol foscarnet/g tissue/h, were calculated from the mean values of the tissue distribution profile using the trapezoidal rule.

TABLE 3

Pharmacokinetic parameters of free and liposomal ddI following the administration of a single intravenous dose (3 mg ddI/kg) in rats.

| Parameters† | Sterically stabilized liposomes DSPC:DSPG:PEG (10:3:1.45) | | Conventional liposomes DSPC:DSPG (10:3) | | Free-ddI |
|---|---|---|---|---|---|
| | [$^3$H]ddI | [$^{14}$C]DPPC | [$^3$H]ddI | [$^{14}$C]DPPC | [$^3$H]ddI |
| $t_{1/2}$ (h) | 3.53 | 14.50 | 2.64 | 3.92 | 0.14 |
| $AUC_{0-\infty}$ (nmol/ml/h) | 950.3 | 17420 | 649.9 | 4971 | 5.31 |
| $K_{el}$ (h$^{-1}$) | 0.20 | 0.048 | 0.26 | 0.18 | 4.97 |
| $Vd_{ss}$ (l/kg) | 0.071 | 0.077 | 0.074 | 0.070 | 0.48 |
| Cl (l/h/kg) | 0.013 | 0.004 | 0.020 | 0.013 | 2.39 |
| MRT (h) | 5.31 | 21.04 | 3.79 | 5.51 | 0.20 |

Parameters were calculated from the plasma concentration-time curves using a noncompartmental model.
†Abbreviations: $t_{1/2}$, elimination half-life; $AUC_{0-\infty}$, area under the plasma concentration-time curve from zero to infinity; $K_{el}$, elimination rate constant; $Vd_{ss}$, steady state volume of distribution; Cl, systemic clearance; MRT, mean residence time.

TABLE 4

Pharmacokinetic parameters of free and liposome-encapsulated PFA following the administration of a single intravenous dose (10 mg/kg) in rats.

| Pharmacokinetic parameters$^a$ | Free foscarnet [$^{14}$C]-PFA | Liposomal foscarnet [$^{14}$C]-PFA | Liposomal lipids [$^3$H]-DPPC |
|---|---|---|---|
| $t_{1/2}$ (h) | 0.71 ± 0.04 | 3.06 ± 0.34 | 5.44 ± 0.79 |
| $AUC_{0-\infty}$ (nmol/ml/h) | 48.0 ± 9.6 | 3687.5 ± 374.2 | 24277.8 ± 2962.8 |
| $K_{el}$ (h$^{-1}$) | 0.96 ± 0.06 | 0.24 ± 0.03 | 0.12 ± 0.02 |
| $Vd_{ss}$ (l/kg) | 0.80 ± 0.14 | 0.040 ± 0.004 | 0.050 ± 0.003 |
| Cl (l/h/kg) | 0.77 ± 0.15 | 0.010 ± 0.001 | 0.006 ± 0.001 |
| MRT (h) | 1.04 ± 0.07 | 4.52 ± 0.42 | 7.93 ± 1.12 |

Values are expressed as means ± SD obtained from 6 animals per group per time point.
$^a$Abbreviations: $t_{1/2}$, elimination half-life; $AUC_{0-\infty}$, area under the plasma concentration-time curve from zero to infinity; $K_{el}$, elimination rate constant; $Vd_{ss}$, steady state volume of distribution; Cl, systemic clearance; MRT, mean residence time.

What is claimed is:

1. A liposome for the treatment of a viral disease which comprises: 1) a lipid component comprising a mixture of diacylphosphatidylcholine and diacylphosphatidylglycerol in a molar ratio ranging between 10:1 and 1:1, wherein the acyl chains are either saturated or unsaturated and have between 16 and 18 carbon atoms in length and ii) a therapeutic amount of an entrapped drug effective against said viral disease.

2. The liposome according to claim 1 wherein said lipid component further comprises a polyethyleneglycol derivative of a diacylphosphatidylethanolamine.

3. A liposome for the treatment of a viral disease which comprises:
   1) a lipid component comprising a mixture of diacylphosphatidylcholine:dicetylphosphate:cholesterol in a molar ratio of 4:1:5, wherein the acyl chains are either saturated or unsaturated and have between 16 and 18 carbon atoms in length and ii) a therapeutic amount of an entrapped drug effective against said viral disease.

4. The liposome according to claim 3 wherein said lipid component further comprises a polyethyleneglycol conjugated to a diacylphosphatidylethanolamine.

5. The liposome of liposomes according to claim 1 wherein the entrapped drug is selected from the group consisting of 3'-azido-3'deoxythymidine (AZT), ddI, ddC, foscarnet, ribavirin, ganciclovir and saquinavir.

6. The liposome of liposomes according to claim 5 wherein the lipid component is diacylphosphatidylcholine:diacylphosphatidylglycerol in a molar ratio of 10:3.

7. The liposome according to claim 2 wherein the entrapped drug is selected from the group consisting of 3'-azido-3'-deoxythymidine (AZT), ddI, ddC, foscarnet, ribavirin, ganciclovir and saquinavir.

8. The liposome according to claim 7 wherein the lipid component is diacylphosphatidylcholine: diacylphosphatidylglycerol:diacylphosphatidylethanolaminepolyethyleneglycol in a molar ratio of 10:3:1:45.

9. The liposome according to claim 3 wherein the entrapped drug is selected from the group consisting of 3'-azido-3'deoxythymidine (AZT), ddI, ddC, foscarnet, ribavirin, ganciclovir and saquinavir.

10. The liposome according to claim 4 wherein the entrapped drug is selected from the group consisting of 3'-azido-3'deoxythymidine (AZT), ddI, ddC, foscarnet, ribavirin, ganciclovir and saquinavir.

11. The liposome according to any one of the claims 2, 4, 8 or 10 wherein the polyethyleneglycol has a molecular weight of between about 500 and about 5000 daltons.

12. The liposome according to claim 6 wherein the lipid component is distearoylphosphatidylcholine:distearoylphosphatidylglycerol in a molar ratio of 10:3 and the entrapped drug is 2'-3'-dideoxyinosine.

13. The liposome according to claim 8 wherein the lipid component is distearoylphosphatidylcholine:distearoylphosphatidylglycerol:distearoylphosphatidylethanolamine-polyethyleneglycol in a molar ratio of 10:3:1:45 and the entrapped drug is 2'-3'-dideoxyinosine.

14. The liposome according to claim 6 wherein the lipid component is dipalmitoylphosphatidylcholine:dipalmitoylphosphatidylglycerol in a molar ratio of 10:3.

15. The liposome according to claim 9 wherein the lipid component is dipalmitoylphosphatidylcholine:dicetylphosphate:cholesterol in a molar ratio of 4:1:5 and the entrapped drug is 2'-3'-dideoxycytidine.

16. The liposome according to claims 1 or 3 having a mean particle diameter of between about 0.05 and 0.5 µm.

17. The liposome according to claim 11 having a mean particle diameter comprised between about 0.05 and 0.5 µm.

18. A method for the treatment of a viral disease to a subject afflicted thereby comprising the step of administering a formulation of liposomes according to claims 1 or 2 to said subject.

19. A method for the treatment of a viral disease to a subject afflicted thereby comprising the step of administering the liposome according to claim 11 to said subject.

20. A method for the treatment of a viral disease to a subject afflicted thereby comprising the step of administering the liposome according to claim 16 to said subject.

* * * * *

UNITED STATES PATENT AND TRADEMARK OFFICE
CERTIFICATE OF CORRECTION

PATENT NO.: 5,773,027

DATED: June 30, 1998

INVENTOR(S): Michel G. Bergeron and Andre Desorméaux

It is certified that error appears in the above-identified patent and that said Letters Patent is hereby corrected as shown below:

ON THE TITLE PAGE

In the Assignee, please delete "Michael" and insert --Michel--.

In the Assignee, please delete "Michael G. Bergeron, Sillery, Canada" and insert --Infectio Recherche Inc., Sainte-Foy, Canada--.

In column 3, lines 7-8, please delete "and ddC respectively".

In column 3, lines 8-9, please insert --, respectively. Figures 1c and 1d illustrate the accumulation of free and liposomal ddC as a function of time, in U937 cells and RAW 264.7 cells, respectively.--

In column 3, line 9, please delete "(Panel A) and (Panel B).".

In column 3, line 10, please delete "1c" and insert --1e--.

In column 3, line 10, please delete "1d" and insert --1f--.

In column 3, line 23, please delete "FIG." and insert --FIGS.--.

In column 3, line 23, after 3a, insert --3b and 3c--.

In column 3, line 23, please delete "represents" and insert --represent--.

In column 3, line 24, please delete "(Panel A)" and insert --(Figure 3a)--.

In column 3, line 24, please delete "(Panel B)" and insert --(Figure 3b)--.

In column 3, line 25, please delete "(Panel C)" and insert --(Figure 3c)--.

UNITED STATES PATENT AND TRADEMARK OFFICE
CERTIFICATE OF CORRECTION

PATENT NO. : 5,773,027

DATED : June 30, 1998

INVENTOR(S) : Michel G. Bergeron and Andre Desormeaux

It is certified that error appears in the above-identified patent and that said Letters Patent is hereby corrected as shown below:

In column 3, line 29, please delete "FIG." and insert --FIGS.--.

In column 3, line 29, please delete "3b" and insert --3d and 3e--.

In column 3, line 29, please delete "represents" and insert --represent--.

In column 3, line 30, please delete "(Panel A)" and insert --(Figure 3d)--.

In column 3, line 30, please delete "(Panel B)" and insert --(Figure 3e)--.

In column 3, line 35, please delete "FIG." and insert --FIGS.--.

In column 3, line 35, please delete "3c" and insert --Figures 3f to 3l--.

In column 3, line 35, please delete "represents" and insert --represent--.

In column 3, line 36, please delete "(Panels A and C) and insert --(Figures 3f and 3h)--.

In column 3, line 37, please delete "(Panels B and D)" and insert --(Figures 3g and 3i)--.

In column 3, lines 37-38, please delete "(Panels A and B)" and insert --(Figures 3f and 3g)--.

In column 3, line 38, please delete "(Panels C and D)" and insert --(Figures 3h and 3i)--.

UNITED STATES PATENT AND TRADEMARK OFFICE
CERTIFICATE OF CORRECTION

PATENT NO. : 5,773,027

DATED : June 30, 1998

INVENTOR(S) : Michel G. Bergeron and Andre Desmoréaux

It is certified that error appears in the above-identified patent and that said Letters Patent is hereby corrected as shown below:

In column 3, line 42, please delete "FIG." and insert --FIGS.--

In column 3, line 42, please delete "3d" and insert --3j to 3l--.

In column 3, line 42, please delete "shows" and insert --show--.

In column 3, line 43, please delete "(Panel A)" and insert --(Figure 3j)--.

In column 3, line 43, please delete "(Panel B)" and insert --(Figure 3k)--.

In column 3, line 44, please delete "(Panel C)" and insert --(Figure 3l)--.

Figure 1B:
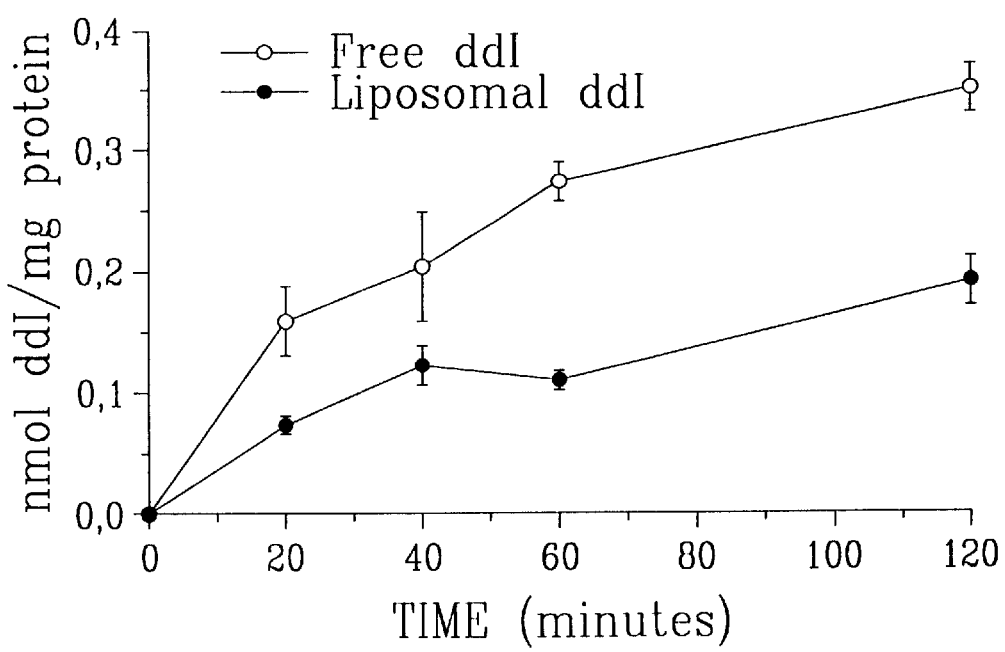
Figure 1C:
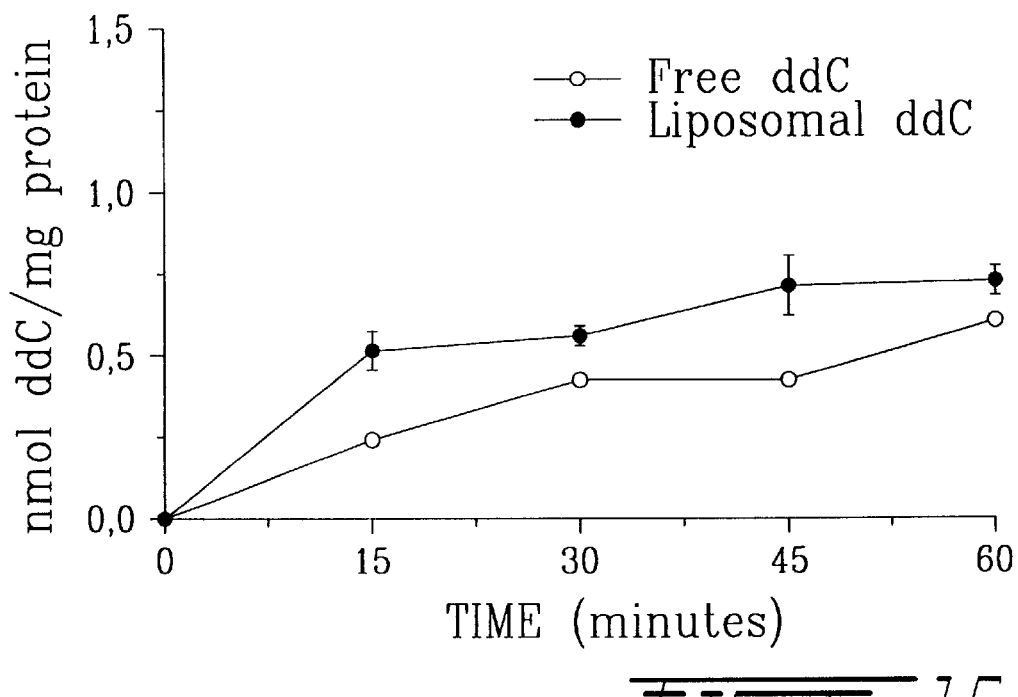
FIGS. 1c and 1d illustrate the accumulation of free and liposomal ddC and foscarnet, respectively, as a function of drug concentration in RAW 264.7 cells.
Figure 1D:
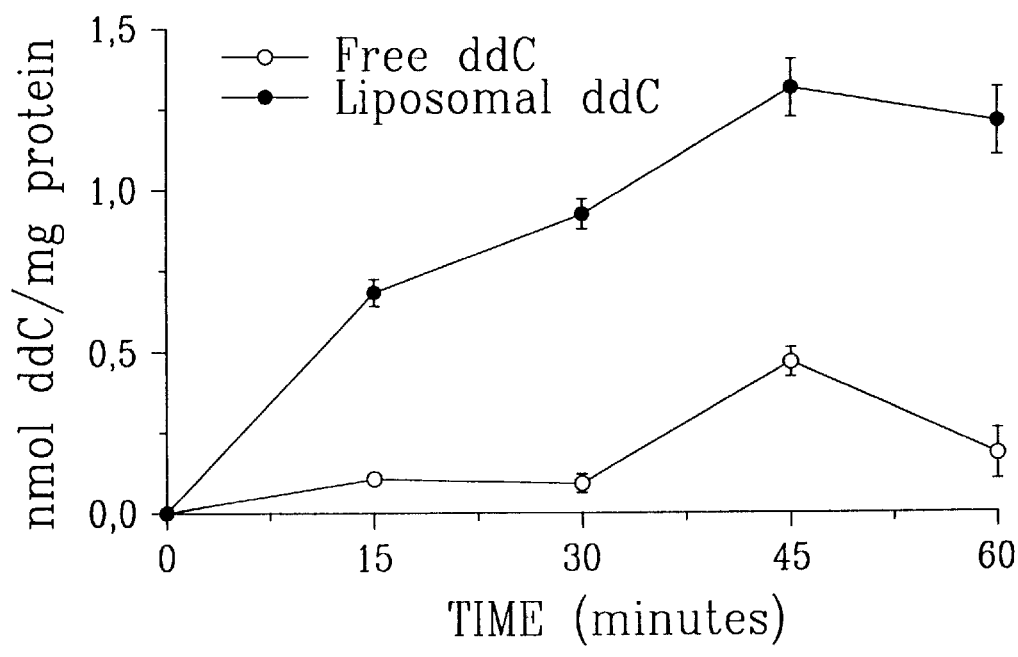
Figure 1E:
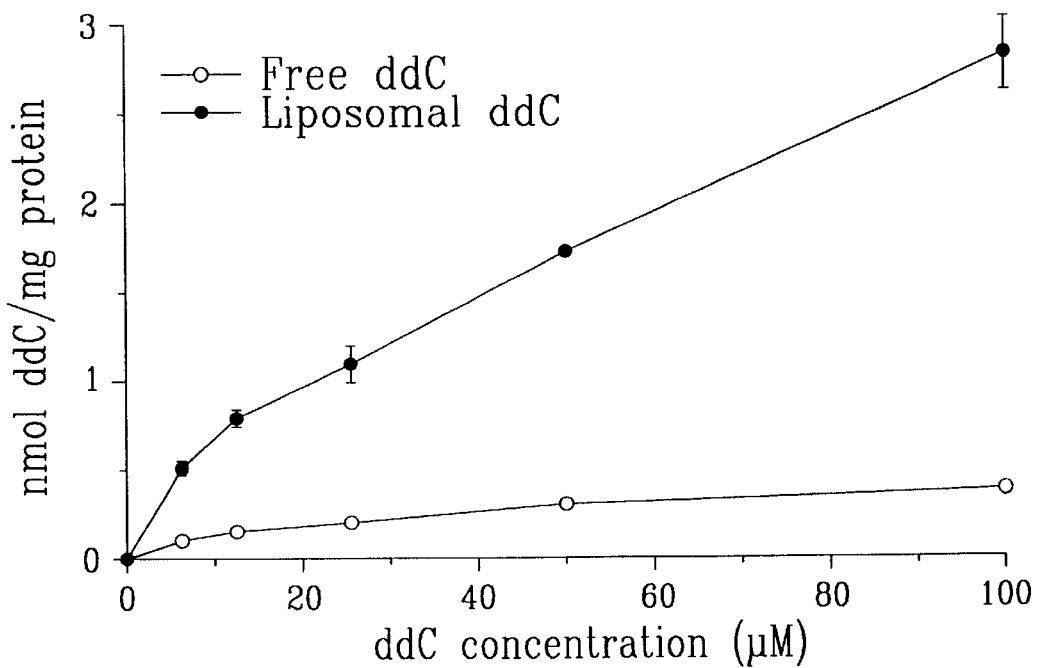
Figure 1F:
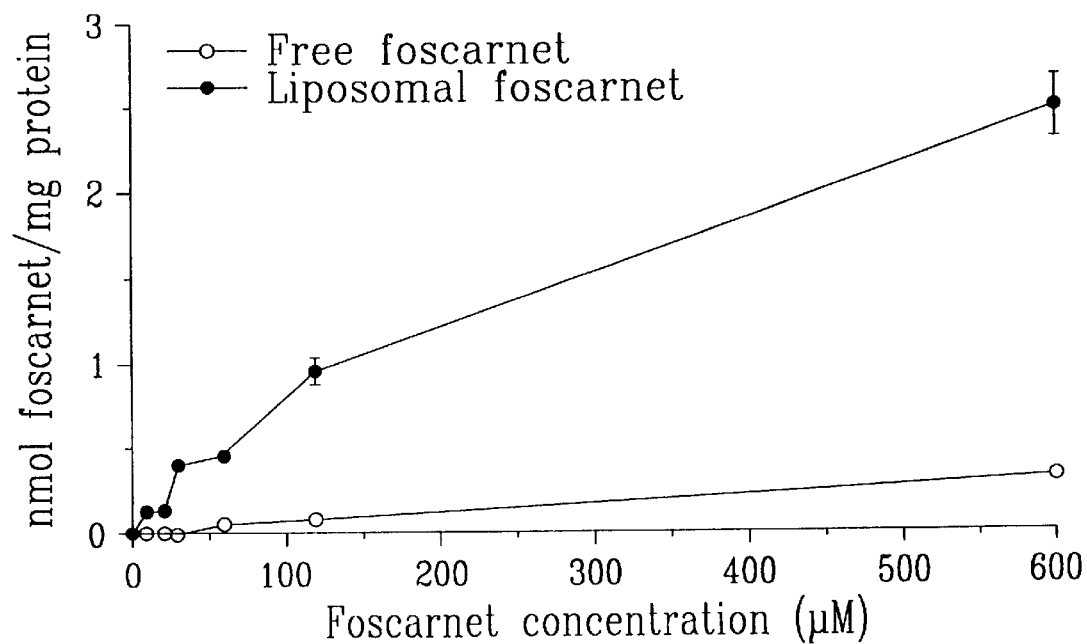

In column 7, lines 6-7, please delete "(Figs. 1b and 1c)" and insert --Figures 1c to 1e--

In column 7, line 8, please delete "(Fig.1d)" and insert --1f--.

In column 7, line 12, please delete (Fig.1a) and insert --Figures 1a and 1b--.

In column 7, line 57, please delete "eficacy" and insert --efficacy--.

In column 8, line 2, please delete "eficacy" and insert --efficacy--.

In column 8, lines 50-51, please delete "3b, 3c and 3d" and insert --to 3l--.

Figure 3A:
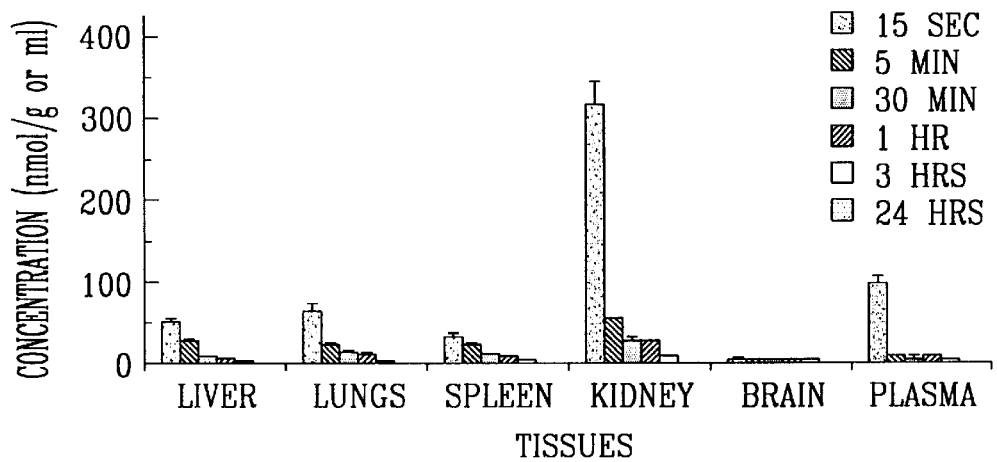
FIG. 3a represents the plasma and tissue distribution of free ddI (Panel A), liposomal ddI (Panel B) and liposomal lipids (Panel C) in rats after the administration of free ddI and ddI entrapped in liposomes composed of DSPC:DSPG in a molar ration of 10:3 and having a mean size particle diameter of 0.175 µm.
Figure 3B:
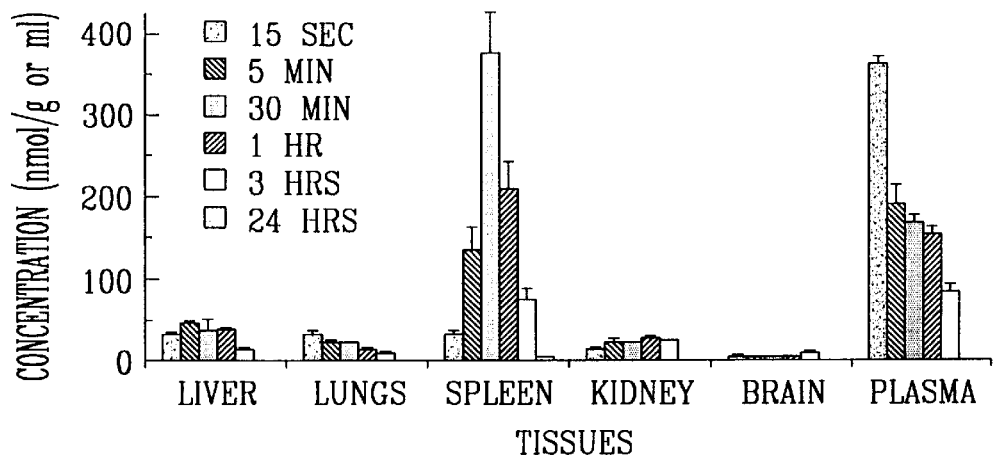
FIG. 3b represents the plasma and tissue distribution of liposomal ddI (Panel A) and liposomal lipids (Panel B) in rats after the administration of ddI entrapped in liposomes composed of DSPC:DSPG:DSPE-PEG in a molar ration of 10:3:1.45 and having a mean size particle diameter of 0.150 µm.
Figure 3C:
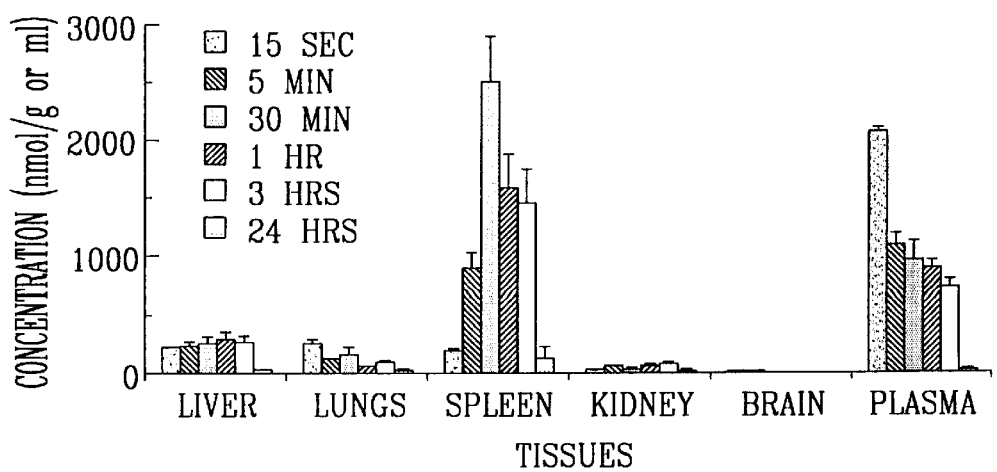
FIG. 3c represents the plasma and tissue distribution of free and liposomal ddC in rats, 1 hour (Panels A and C) and 3 hours (Panels B and D) after the intravenous (Panels A and B) or intraperitoneal (Panels C and D) administration of free ddC and ddC entrapped in liposomes composed of DPPC:DP:CHOL in a molar ration of 4:1:5 and having a mean size particle diameter of 0.300 µm.
Figure 3D:
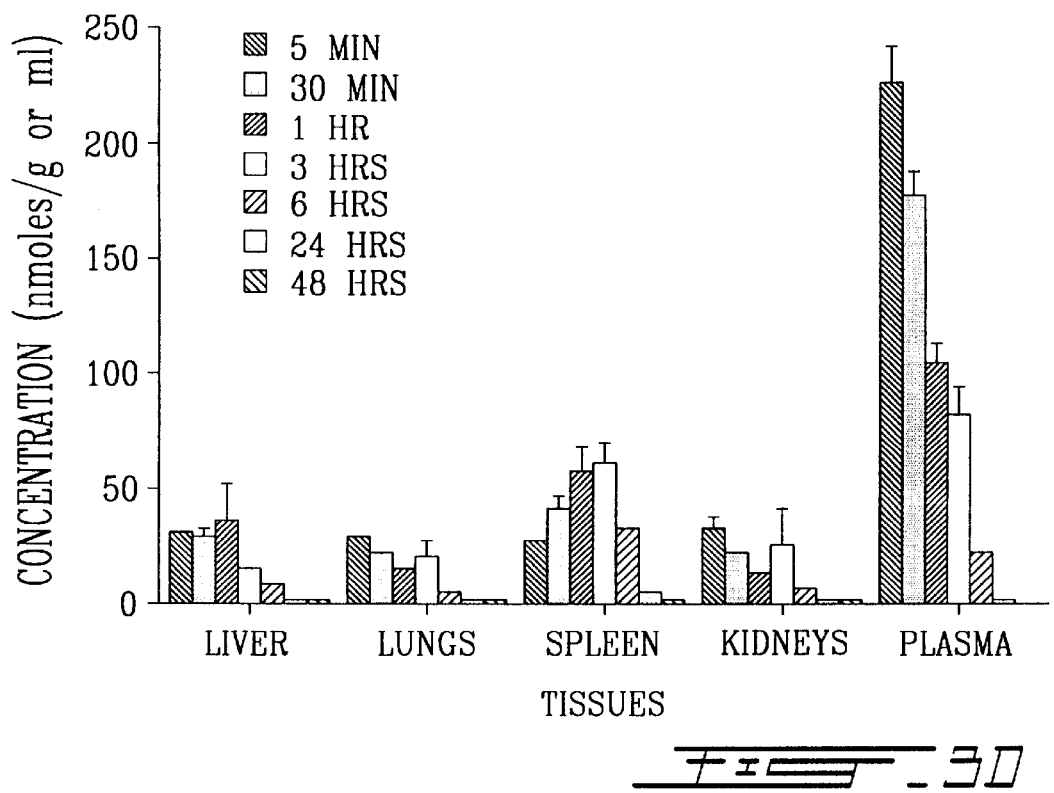
FIG. 3d shows the plasma and tissue distribution of liposomal foscarnet (Panel A), free foscarnet (Panel B) and liposomal lipids (Panel C) in rats after the administration of free foscarnet or foscarnet entrapped in liposomes composed of DPPC:DPPG in a molar ration of 10:3 and having a mean size particle diameter of 0.165 µm.
Figure 3E:
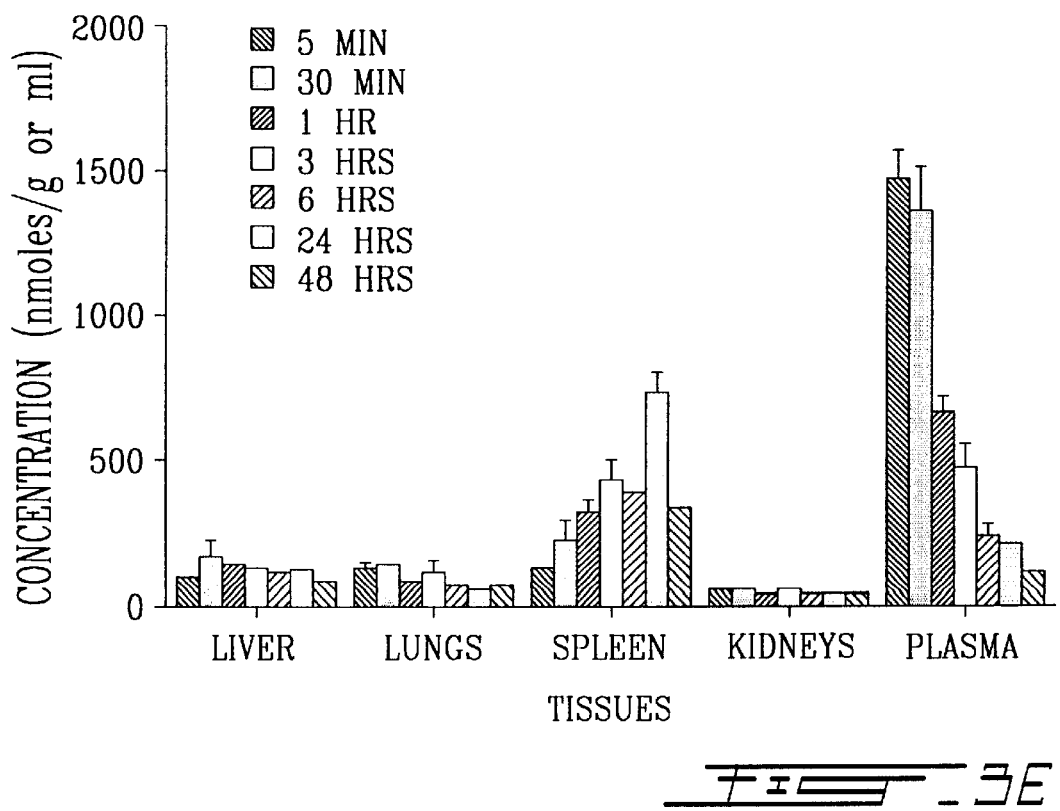
Figure 3F:
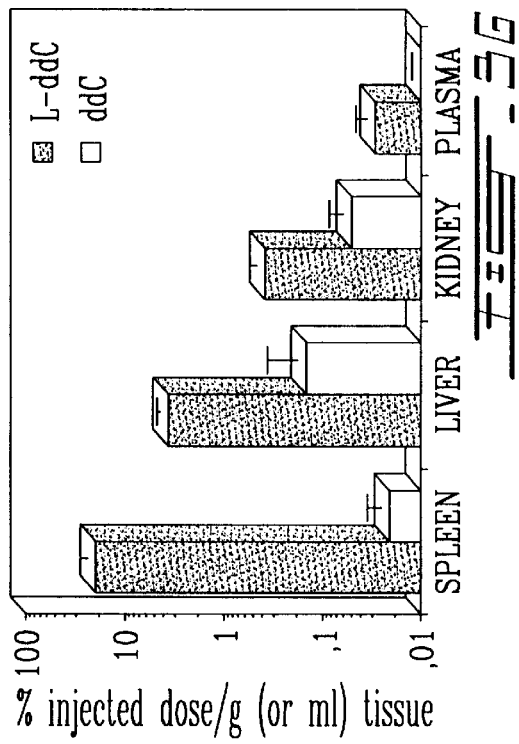
Figure 3G:
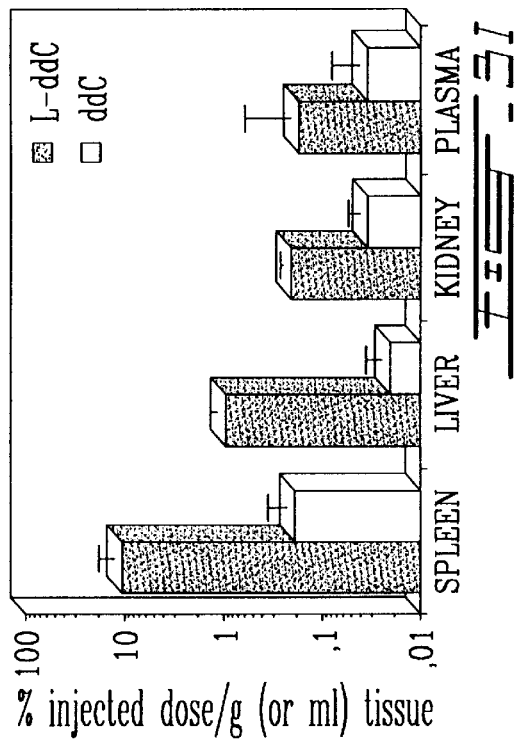
Figure 3H:
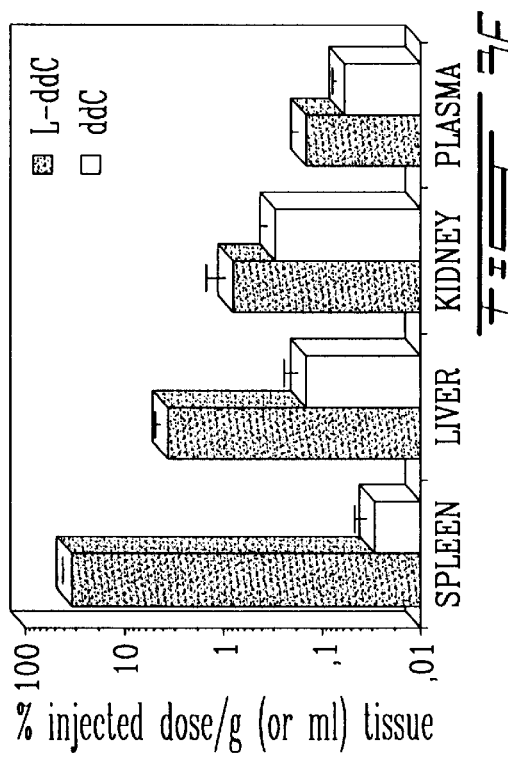
Figure 3I:
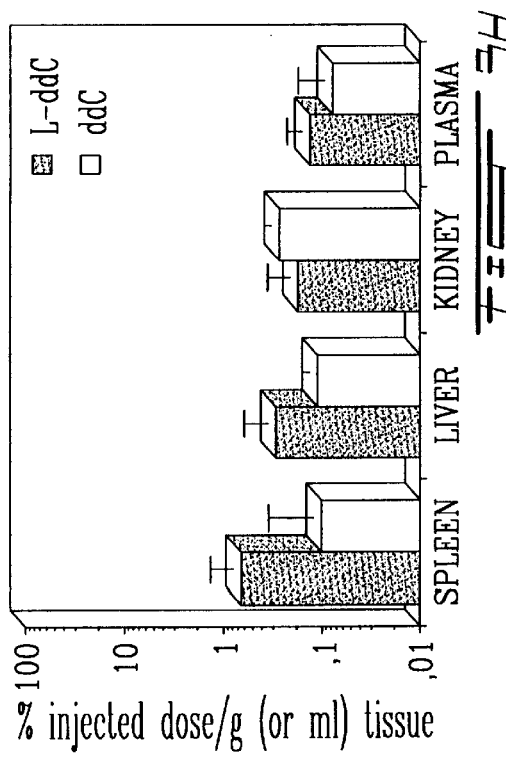
Figure 3J:
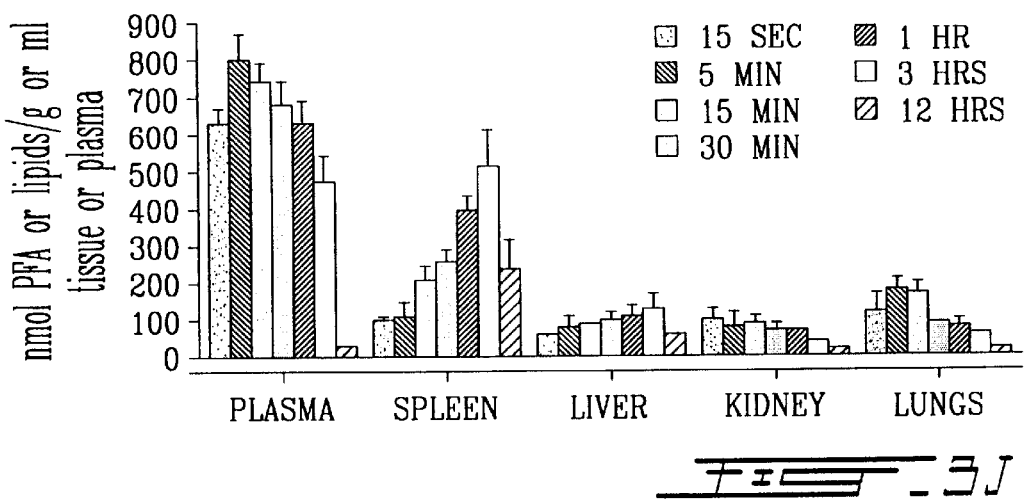
Figure 3K:
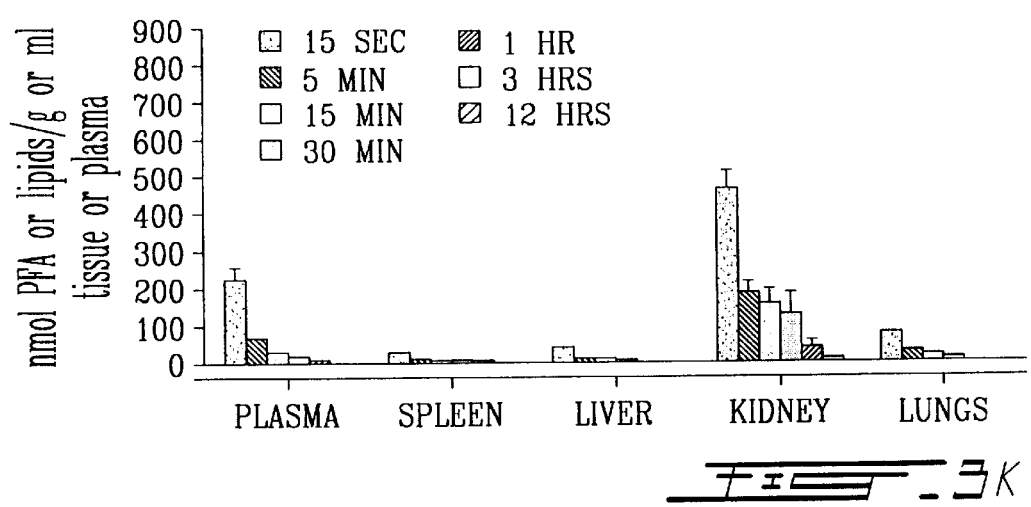
Figure 3L:
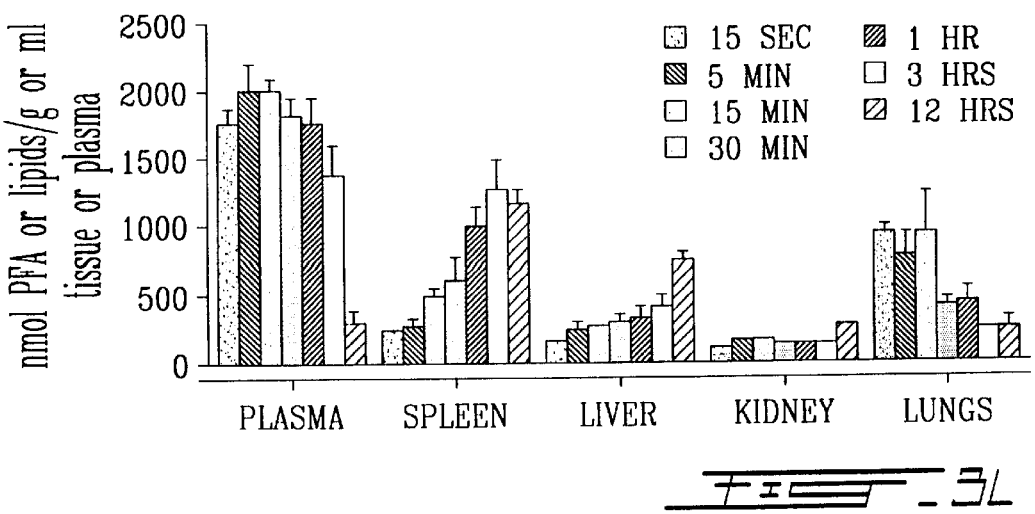

In column 8, line 58, please delete "Fig. 3d" and insert --3j to 3l--.

In column 9, lines 3-4, please delete "3b and 3d" and insert --to 3e and 3j to 3l--.

UNITED STATES PATENT AND TRADEMARK OFFICE
CERTIFICATE OF CORRECTION

PATENT NO. : 5,773,027

DATED : June 30, 1998

INVENTOR(S) : Michel G. Berferon and Andre Desormeaux

It is certified that error appears in the above-identified patent and that said Letters Patent is hereby corrected as shown below:

In column 10, line 23, please delete "ii)" and insert --2--.

In column 10, lines 27-28, please delete "derivative of a" and insert --conjugated to--.

In column 10, line 35, please delete "ii)" and insert --2--.

In column 10, line 39, please delete "a".

In column 10, line 40, please delete "of liposomes".

In column 10, line 44, please delete "of liposomes".

In column 12, line 7, please delete "formulation of".

In column 12, line 7, please delete "liposomes" and insert --liposome--.

Signed and Sealed this

Twenty-ninth Day of May, 2001

*Attest:*

NICHOLAS P. GODICI

*Attesting Officer*  *Acting Director of the United States Patent and Trademark Office*